US008806938B2

(12) United States Patent
Kondo

(10) Patent No.: US 8,806,938 B2
(45) Date of Patent: Aug. 19, 2014

(54) SPECIFIC GRAVITY MEASURING APPARATUS

(75) Inventor: Sadanori Kondo, Osaka (JP)

(73) Assignee: Alfa Mirage Co., Ltd. (JP)

( * ) Notice: Subject to any disclaimer, the term of this patent is extended or adjusted under 35 U.S.C. 154(b) by 338 days.

(21) Appl. No.: 13/359,280

(22) Filed: Jan. 26, 2012

(65) Prior Publication Data

US 2013/0086984 A1    Apr. 11, 2013

(30) Foreign Application Priority Data

Oct. 6, 2011    (JP) .................................. 2011-221503

(51) Int. Cl.
*G01N 9/10*    (2006.01)
*G01N 9/36*    (2006.01)
*G01N 9/08*    (2006.01)

(52) U.S. Cl.
CPC ... *G01N 9/36* (2013.01); *G01N 9/08* (2013.01)
USPC .............................................. 73/437; 73/433

(58) Field of Classification Search
USPC ............ 73/32 R, 433, 437; 177/207; 209/259
See application file for complete search history.

(56) References Cited

U.S. PATENT DOCUMENTS

| 3,747,416 | A | * | 7/1973 | Wommack | 73/437 |
| 4,372,405 | A | * | 2/1983 | Stuart | 177/25.14 |
| 4,770,041 | A | * | 9/1988 | Bearce | 73/437 |
| 6,561,025 | B2 | * | 5/2003 | Ueno | 73/437 |
| 7,296,466 | B2 | * | 11/2007 | Kusumoto | 73/437 |

FOREIGN PATENT DOCUMENTS

| CN | 1161597 C | 8/2004 |
| DE | 10205887 B4 | 5/2008 |
| JP | 4049571 Y2 | 11/1992 |
| JP | 2002243615 | * 8/2002 |

* cited by examiner

*Primary Examiner* — Hezron Williams
*Assistant Examiner* — Hoang Nguyen
(74) *Attorney, Agent, or Firm* — St. Onge Steward Johnston & Reens LLC

(57) ABSTRACT

A specific gravity measuring apparatus includes a liquid bath, a measured object receiving member which is housed in the liquid bath via a support means in a non-contact manner and into and out of which a liquid within the liquid bath can freely flow, an aerial mounting member which is supported by the support means and on which a measured object is placed in order to measure gravity thereof in the air, and a weighing apparatus receiving and supporting the measured object receiving member via the support means. The weighing apparatus 5 is provided with a sensor and a measuring section. The aerial mounting member is provided in such a manner as to cover a part of an opening O at an upper part of the liquid bath.

15 Claims, 5 Drawing Sheets

SPECIFIC GRAVITY MEASURING APPARATUS

CROSS-REFERENCE TO RELATED APPLICATIONS

The present application claims priority of Japanese patent application No. 2011-221503 filed on Oct. 6, 2011, the content of which is incorporated herein by reference.

FIELD OF THE INVENTION

The present invention relates to a specific gravity measuring apparatus for measuring specific gravity of solids and is used to find purity of, for example, gold and platinum or physical properties of solids such as rubber, plastic, etc.

BACKGROUND OF THE INVENTION

Conventional specific gravity measuring apparatuses include one which is described in Japanese examined utility model registration publication No. H04-49571. This specific gravity measuring apparatus is composed of a liquid bath filled with a liquid, a measured object receiving member which is housed in the liquid bath via a support means in a non-contact manner and into and out of which the liquid within the liquid bath can freely flow, an aerial mounting member which is supported by the support means and on which a measured object is placed in order to measure gravity thereof in the air, and a weighing apparatus which receives and supports the measured object receiving member via the support means, wherein the weighing apparatus is provided with a sensor which converts a weight acted upon the measured object receiving member into an electrical signal and a measuring section which measures specific gravity of the measured object from an output of the sensor at the time when the measured object is placed on the aerial mounting member and an output of the sensor at the time when the measured object is submerged and placed on the measured object receiving member, and the aerial mounting member comprises a lid body attached to the support means so as to fully open and close an opening at an upper part of the liquid bath. To use this specific gravity measuring apparatus, the aerial mounting member comprising the lid body is attached to close the opening at the upper part of the liquid bath. In this state, the measured object is placed on the aerial mounting member, and a weight in air of the object is measured. After that, the aerial mounting member is detached from the support means to open the upper opening of the liquid bath. In this state, the measured object is sunk into water and placed on the measured object receiving member. Then, the aerial mounting member is closed again, and in this state, a weight in water of the measured object is measured. The specific gravity of the measured object is measured by a difference between the weight in air and the weight in water of the measured object having been measured in the afore-described manner.

SUMMARY OF THE INVENTION

In the above conventional specific gravity measuring apparatus, the aerial mounting member comprising the lid body needs to be opened and closed in using the apparatus. In addition to that the opening and closing operation is troublesome, the opening and closing action of the aerial mounting member gives a physical shock to the interior of the weighing apparatus. This can disadvantageously cause subtle variations in measured values and reduce specific gravity measurement accuracy.

In view of the afore-described circumstances, the present invention aims at providing a specific gravity measuring apparatus which does not need to open and close the aerial mounting member each time and can improve specific gravity measurement accuracy. Described with reference symbols of an embodiment described later just for reference, a specific gravity measuring apparatus as set forth in claim 1 includes a liquid bath 1 filled with a liquid L, a measured object receiving member 3 which is housed in the liquid bath 1 via a support means 2 in a non-contact manner and into and out of which the liquid L within the liquid bath 1 can freely flow, an aerial mounting member 4 which is supported by the support means 2 and on which a measured object M is placed in order to measure gravity thereof in the air, and a weighing apparatus 5 receiving and supporting the measured object receiving member 3 via the support means 2, the weighing apparatus 5 being provided with a sensor 6 converting a weight acted upon the measured object receiving member 3 into an electrical signal and a measuring section 7 measuring specific gravity of the measured object M from an output of the sensor 6 at the time when the measured object M is placed on the aerial mounting member 4 and an output of the sensor 6 at the time when the measured object M is submerged and placed on the measured object receiving member 3, wherein the aerial mounting member 4 is provided in such a manner as to cover a part of an opening O at an upper part of the liquid bath 1 and leave the remainder open but not to fully cover the opening O, and the measured object M having been placed on the mounting member 4 can be dropped onto the measured object receiving member 3 directly.

According to the thus configured specific gravity measuring apparatus of the present invention, the aerial mounting member 4 is provided in such a manner as to cover a part of the opening O at the upper part of the liquid bath 1 and leave the remainder open but not to fully cover the opening O as in the conventional specific gravity measuring apparatus, and the measured object M having been placed on the mounting member 4 can be dropped onto the measured object receiving member 3 directly. Thus, there is no need to open and close the aerial mounting member each time as in the conventional apparatus, and accordingly, labor of the opening and closing operation of the aerial mounting member can be saved and tasks can be performed easily. In addition, no physical shock is given to the interior of the weighing apparatus 5, so that the possibility of causing subtle variations in measured values is eliminated and specific gravity measurement accuracy can be improved.

To carry out the above-configured present invention, more specifically, as set forth in claim 2, the support means 2 is constituted by a support frame body 13 integrally formed into a substantially square frame shape by four columns 11 and transverse frames 12 connecting the columns 11 together, four cable bodies 14 for hanging and supporting the measured object receiving member 3, the cable bodies 14 being hung down from respective upper ends of the columns 11 of the square frame-shaped support frame body 13, and a bottom frame body 15 fixed to a receiving portion 6a of the sensor 6 of the weighing apparatus 5 and supporting lower ends of the columns 11 of the square frame-shaped support frame body 13. By thus configuring the support means 2, the structure thereof is simplified and a reduction in weight thereof can be achieved. As a result, the measurement accuracy can be improved, and assembly and disassembly of the support means 2 can be facilitated.

Further, as set forth in claim 3, the columns 11 of the square frame-shaped support frame body 13 of the support means 2 have upper ends provided with four support arms 16 in a diagonal direction of the support frame body 13. The support arms 16 have distal ends from which protruding portions 16*a* are protruded, and to the protruding portions 16*a*, upper ends of the cable bodies 14 are fixed. The cable bodies 14 have lower ends fixed to protruding portions 3*d* provided at necessary places of an outer periphery of the measured object receiving member 3, and the measured object receiving member 3 is hung and supported by those four cable bodies 14. Accordingly, installation operation of the measured object receiving member 3 by the cable bodies 14 is facilitated. Further, as set forth in claim 4, the measured object receiving member 3 is composed of a bottom plate 3*a* and a peripheral wall 3*b* projected along a peripheral edge of the bottom plate 3*a*, and the bottom plate 3*a* is provided with a plurality of through holes 3*c*. By such configuration, the measured object receiving member 3 can easily be formed by, for example, plastic molding.

As set forth in claim 5, the aerial mounting member 4 is configured to have a proximal end pivotally fitted to the support means 2 and change its posture between a horizontal posture of covering a part of the opening O and a rising posture of rising from the horizontal posture. With this configuration, storing operation of the liquid bath 1 is simplified and facilitated by bringing the aerial mounting member 4 into the rising posture when the liquid bath 1 is stored within the support means 2 prior to the use of the specific gravity measuring apparatus. As set forth in claim 6, a configuration is employed that the aerial mounting member 4 is composed of a flat plate 4*a* and a measured object mounting portion 4*b* integrally projected along the flat plate 4*a* from a center of a distal end of the flat plate 4*a* and formed into a gentle concave dished shape and that the measured object M is placed on this gentle concave dish-shaped measured object mounting portion 4*b*. With that, unfavorable situations such as an accidental rolling-down of the measured object M from the aerial mounting member 4 can be prevented as long as the measured object measured object M is placed on the concave dish-shaped measured object mounting portion 4*b* at the time of measurement. Further, since the concave dish-shaped measured object mounting portion 4*b* is of a gentle concave dished shape, there is no problem in dropping the measured object M into the liquid bath 1, and the measured object M can be dropped easily. Moreover, as set forth in claim 7, if a configuration is employed that the aerial mounting member 4 has a distal end to which an extension member 24 formed in such a size that covers the remainder of the opening O and extending the aerial mounting member 4 is detachably connected so as to be flush with the aerial mounting member 4, a measured object M too large to be mounted on the aerial mounting member 4 can be placed and a measurement thereof can be carried out.

DETAILED DESCRIPTION OF THE INVENTION

Figure 1:
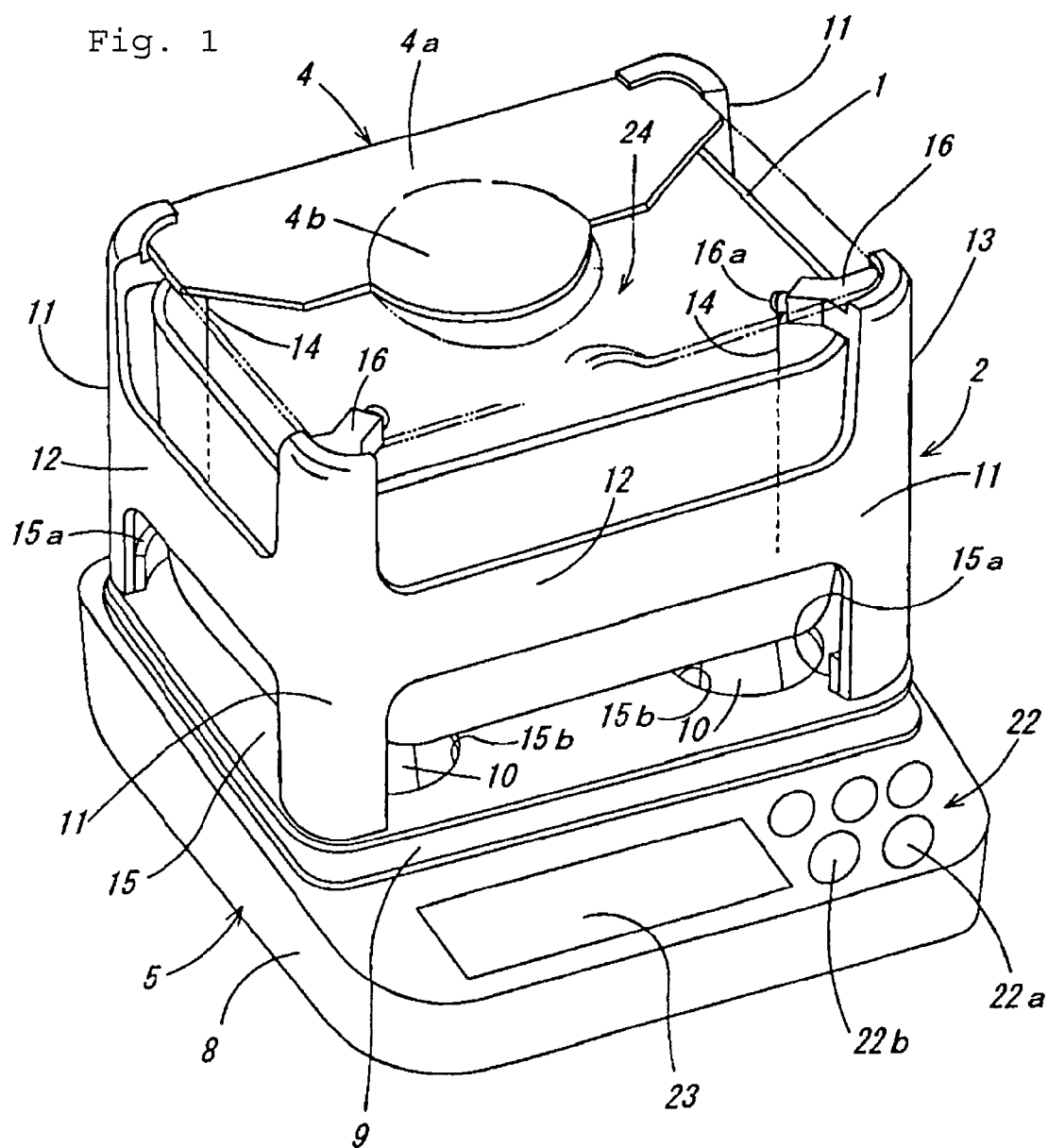
FIG. 1 is an exterior perspective view of a specific gravity measuring apparatus according to the present invention seen from the front.
Figure 2A:
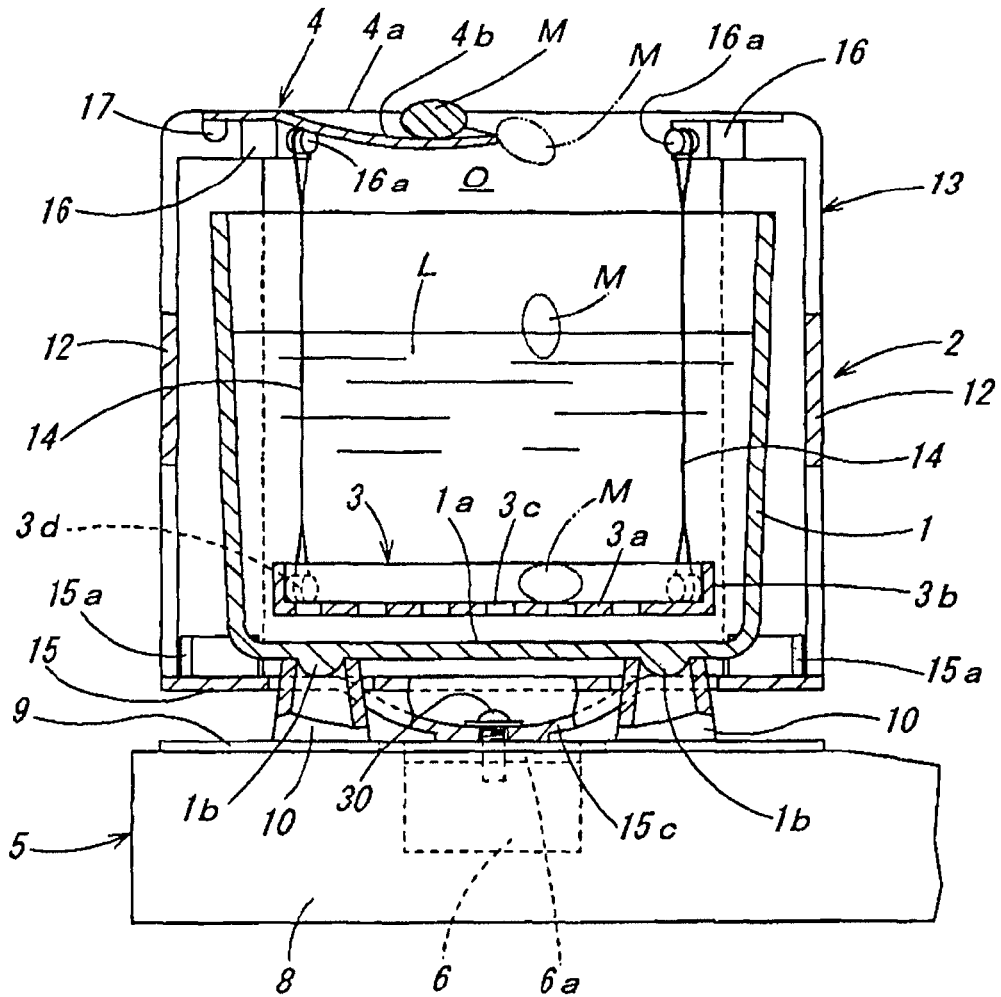
FIG. 2A is a longitudinal sectional side view of the specific gravity measuring apparatus.

Hereinafter, a preferred embodiment of the present invention will be described based on the drawings. In FIG. 1 and FIG. 2A, a specific gravity measuring apparatus includes an angular cylindrical liquid bath 1 filled with a liquid L, a measured object receiving member 3 which is housed in the liquid bath 1 via a support means 2 in a non-contact manner and into and out of which the liquid L within the liquid bath 1 can freely flow, an aerial mounting member 4 which is supported by the support means 2 and on which a measured object M is placed in order to measure gravity thereof in the air, and a weighing apparatus 5 receiving and supporting the measured object receiving member 3 via the support means 2, the weighing apparatus 5 being provided with an electromagnetic-type sensor 6 converting a weight acted upon the measured object receiving member 3 into an electrical signal and a measuring section 7 measuring specific gravity of the measured object M from an output of the sensor 6 at the time when the measured object M is placed on the aerial mounting member 4 and an output of the sensor 6 at the time when the measured object M is submerged and placed on the measured object receiving member 3. This specific gravity measuring apparatus is characterized in that the aerial mounting member 4 is provided in such a manner as to cover a part of an opening O at an upper part of the liquid bath 1 and leave the remainder open but not to fully cover the opening O as in the conventional specific gravity measuring apparatus and that the measured object M having been placed on the aerial mounting member 4 can be dropped onto the measured object receiving member 3 as it is without detaching the aerial mounting member 4.

Figure 3A:
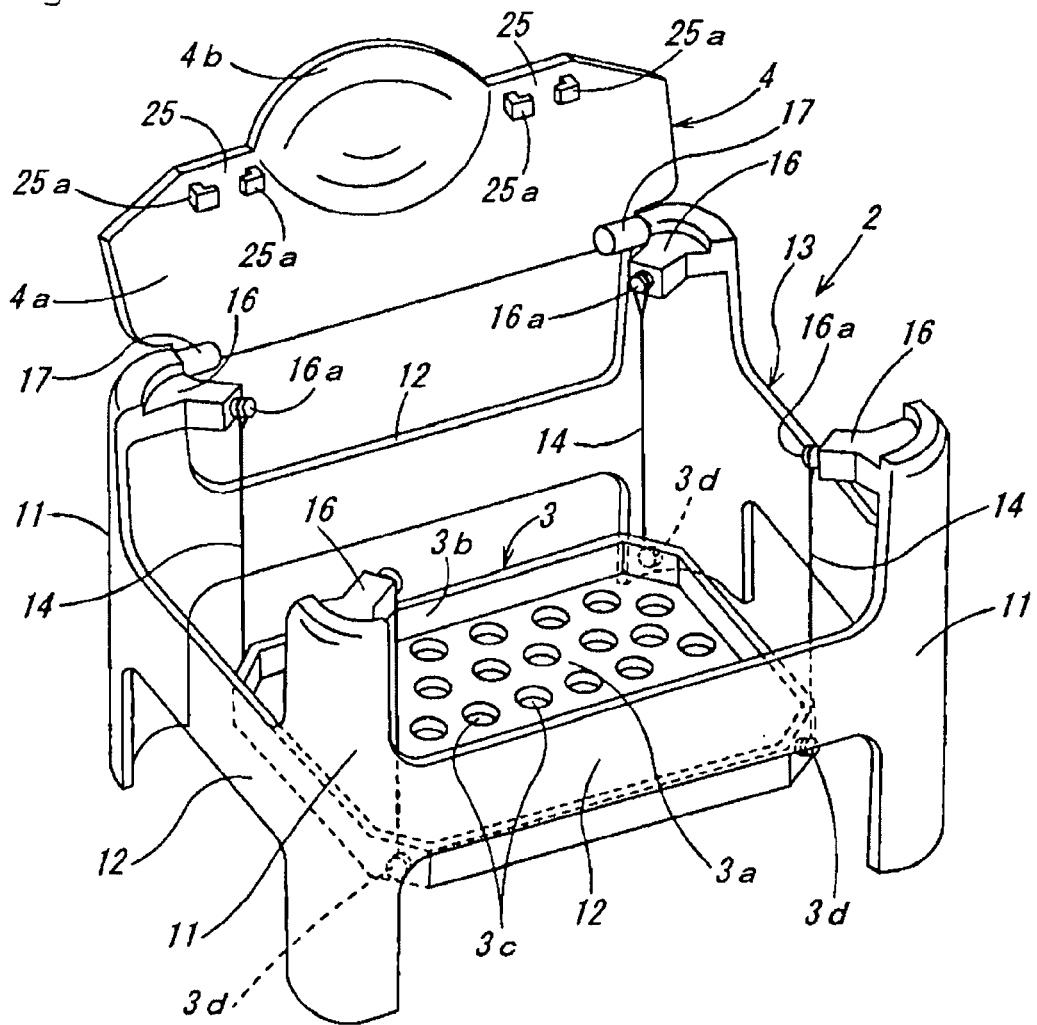
FIG. 3A is a perspective view showing a support means, a measured object receiving member, and an aerial mounting member in a rising posture of the specific gravity measuring apparatus.
Figure 4A:
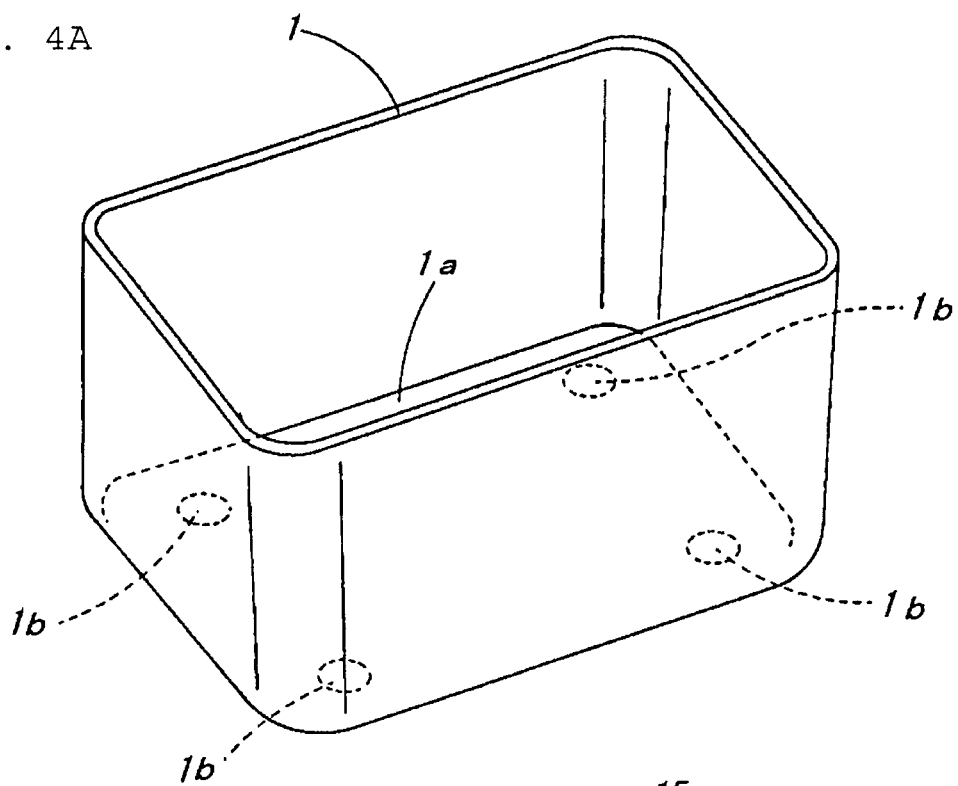
FIG. 4A is a perspective view showing a liquid bath.

The structure of the above specific gravity measuring apparatus will be described in more detail. The liquid bath 1 includes hemispheric protrusions 1*b* respectively downwardly protruding in four corners of the underside of a bottom wall 1*a* as shown in FIG. 2A and FIG. 4A. The hemispheric protrusions 1*b* are engaged with top openings 10*a* (see FIG. 4B) of hollow conical support legs 10 projected on a doughnut-shaped fixed plate 9 fixed on an upper surface of a case 8 of the weighing apparatus 5 and having an opened center, thereby being supported stably. The measured object receiving member 3 is composed of a rectangular bottom plate 3*a* and a peripheral wall 3*b* projected along a peripheral edge of the bottom plate 3*a* as shown in FIG. 2A and FIG. 3A. The bottom plate 3*a* is provided with a plurality of through holes 3*c*.

Figure 4B:
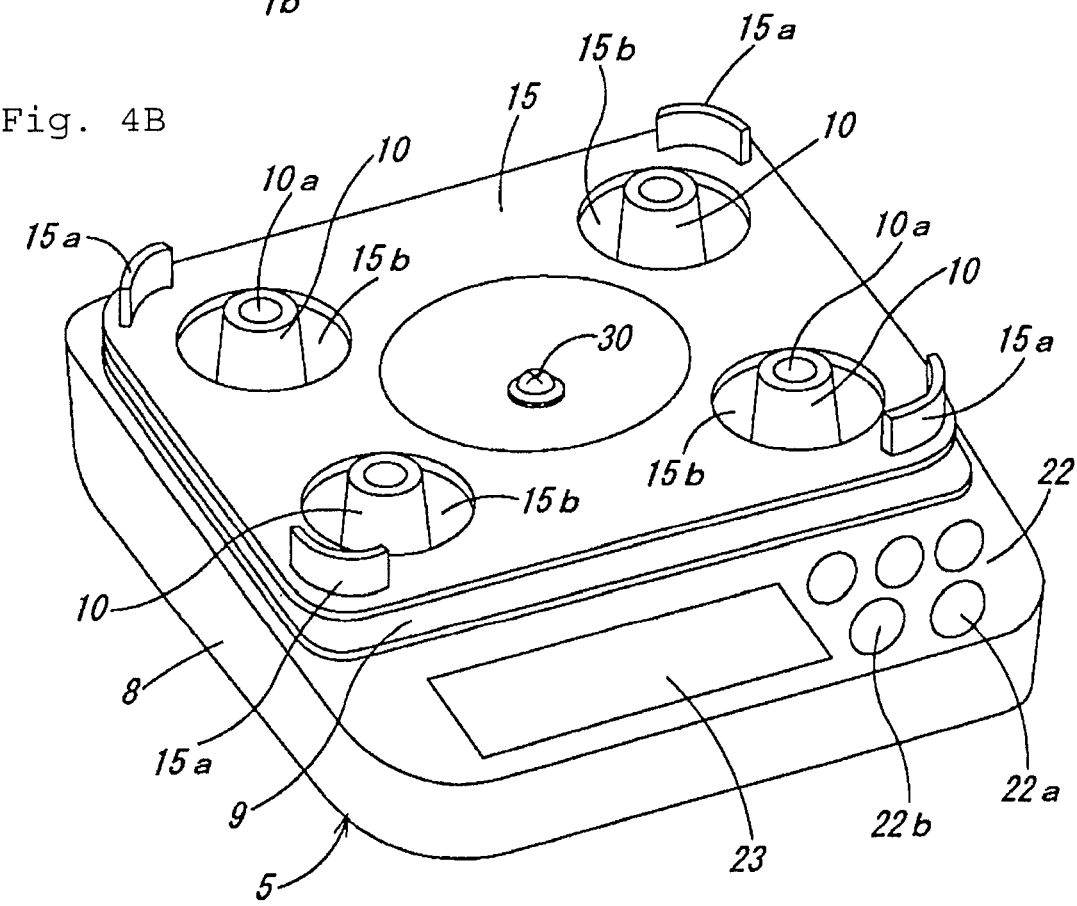
FIG. 4B is a perspective view showing a base of the apparatus.

As shown in FIGS. 2A, 3A and 4B, the support means 2 is constituted by a support frame body 13 integrally formed into a substantially square frame shape by four columns 11 having a circular arc cross section and transverse frames 12 connecting the columns 11 together, four cable bodies 14 for hanging and supporting the measured object receiving member 3, the cable bodies 14 being hung down from respective upper ends of the columns 11 of the square frame-shaped support frame body 13, and a bottom frame body 15 having four corners provided with circular arc fitting walls 15a to which respective lower ends of the columns 11 of the square frame-shaped support frame body 13 are fitted from the outside, the bottom frame body 15 having holes 15b in inner vicinities of the fitting walls 15a for letting through the support legs 10 so as not to contact therewith. The bottom frame body 15 supports the lower ends of the four columns 11 of the square frame-shaped support frame body 13 in the four corners as shown in FIG. 2A. The bottom frame body 15 has a central underside downwardly and convexly projected and, in the center of that projection 15c, the bottom frame body 15 is fixed on a receiving portion 6a of the sensor 6 by a screw 30.

As shown in FIG. 3A, the columns 11 of the square frame-shaped support frame body 13 have upper ends respectively provided with support arms 16 in a diagonal direction of the square frame-shaped support frame body 13. The support arms 16 have distal ends from which protruding portions 16a are protruded, and to the protruding portions 16, upper ends of the cable bodies 14 formed of, for example, a thin metal wire are fixed. The cable bodies 14 have lower ends fixed to protruding portions 3d provided at outer corner portions of four corners of the peripheral wall 3b of the measured object receiving member 3. In this manner, the four cable bodies 14 hang and support the measured object receiving member 3.

Figure 2B:
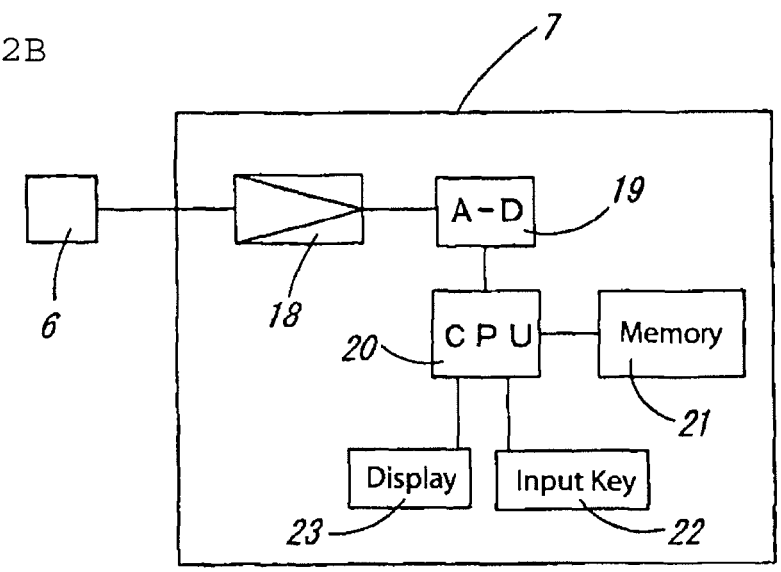
FIG. 2B is a block diagram of the specific gravity measuring apparatus.
Figure 3B:
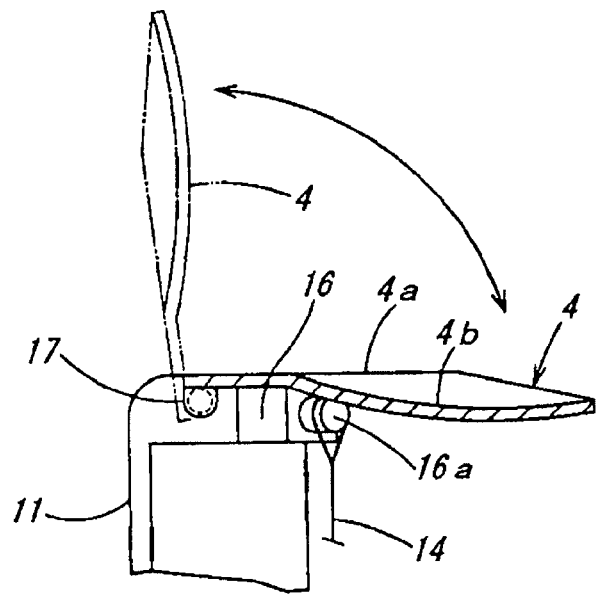
FIG. 3B is a longitudinal sectional side view showing a mounting state of the aerial mounting member.

Referring to FIGS. 1 to 3B, the aerial mounting member 4 is pivotally fitted to the upper ends of adjacent columns 11 of the square frame-shaped support frame body 13 by pivots 17 in such a manner as to planarly cover about a half of the upper opening O of the liquid bath 1 such that the aerial mounting member 4 can change its posture between a horizontal posture of covering the opening O and a rising posture of rising from the horizontal posture. In FIG. 3B, the aerial mounting member 4 in the horizontal posture is shown by a solid line, and the aerial mounting member 4 in the rising posture, by an imaginary line. The aerial mounting member 4 is composed of a flat plate 4a and a measured object mounting portion 4b projected in the center of an inner end of the flat plate 4a and formed into a gentle concave dished shape. The measured object M is designed to be placed on the gentle concave dish-shaped measured object mounting portion 4b (see FIG. 1 and FIG. 2A). Since the aerial mounting member 4 includes the measured object mounting portion 4b formed into a concave dished shape as just described, unfavorable situations such as an accidental rolling-down of the measured object M from the aerial mounting member 4 can be prevented as long as the measured object M is placed on the concave dish-shaped measured object mounting portion 4b at the time of measurement. Additionally, since the concave dish-shaped measured object mounting portion 4b is of a gentle concave dished shape, there is no problem in dropping the measured object M into the liquid bath 1, and the measured object M can be dropped easily.

FIG. 2B illustrates a block diagram of the weighing apparatus 5. Referring to this drawing, a load applied to the bottom frame body 15 of the support means 2 composed of the support frame body 13, the four cable bodies 14, and the bottom frame body 15 is converted into an electrical signal by the electromagnetic-type sensor (electromagnetic sensor) 6, and an output thereof is subjected to various operations in the measuring section 7, whereupon specific gravity is measured and displayed. The measuring section 7 is composed of an amplifier 18 which amplifies the output of the electromagnetic sensor 6 and outputs an analog signal according to the load, an analog-to-digital converter 19 which converts the analog signal to a digital signal, a processing unit (CPU) 20 comprising a microcomputer, a memory 21, an input key 22, and a display 23. It is noted that a load cell can be used as the sensor 6 but the electromagnetic-type sensor (electromagnetic sensor) can calculate values with higher accuracy. Accordingly, the electromagnetic sensor is used herein.

The above-described structure will be described in more detail together with operations. A first key 22a of the input key 22 (see FIG. 1) is pressed in a state where water L is filled within the liquid bath 1 as shown in FIG. 2A and where the measured object M is not placed on the aerial mounting member 4 or entered into the liquid bath 1 yet. An output of the electromagnetic sensor 6 at that moment, that is, a weight A of the measured object receiving member 3, aerial mounting member 4, and support means 2 (composed of the support frame body 13, the cable bodies 14, and the bottom frame body 15) is reset, and "0" is stored in the memory 21 and also displayed at the display 23. Gravity acted upon the measured object receiving member 3 at that moment is the gravity of the measured object receiving member 3, aerial mounting member 4, and support means 2 (support frame body 13, cable bodies 14, and bottom frame body 15) minus buoyancy applied to the measured object receiving member 3 by the water L.

Subsequently, the measured object M is placed on the measured object mounting portion 4b of the aerial mounting member 4 as shown by a solid line in FIG. 2A, whereupon a weight in air thereof is measured and displayed at the display 23. A second key 22b of the input key 22 is pressed in that state, and then the weight in air M1 is stored in the memory 21. After that, the measured object M having been placed on the measured object mounting portion 4b is lightly slid down from the distal end of the measured object mounting portion 4b as shown by an imaginary line in FIG. 2A. The measured object M is received on the measured object receiving member 3 having been sunk in the water L within the liquid bath 1. Then, a weight in water M2 of the measured object M is measured. In parallel with this measurement, the following operation (1) is performed by the processing unit 20, and specific gravity S which is a result of the operation is displayed at the display 23.

$$S = M1/(M1 - M2) \quad (1)$$

It is noted that once the measured object M is lifted up after the object M is placed on the aerial mounting member 4 and the weight in air thereof is measured, the weight in air becomes zero. However, by detecting that, the weight indication is designed to automatically be switched into the specific gravity S indication at the display 23. Further, whether the indication is weight or specific gravity is also displayed.

As understood from the above description of the embodiment, this specific gravity measuring apparatus is configured such that the aerial mounting member 4 is provided in such a manner as to cover a part, for example, about a half of the upper opening O of the liquid bath 1 and leave the remainder open but not to fully cover the opening O as in the conventional specific gravity measuring apparatus and such that the measured object M having been placed on the mounting member 4 can be dropped onto the measured object receiving member 3 directly. Since there is no need to open and close the aerial mounting member each time as in the conventional apparatus, labor of the opening and closing operation of the aerial mounting member can be saved and tasks can be carried out easily. Additionally, no physical shock is given to the interior of the weighing apparatus 5, so that the possibility of causing subtle variations in measured values is eliminated. As a result, specific gravity measurement accuracy can be improved.

Figure 5A:
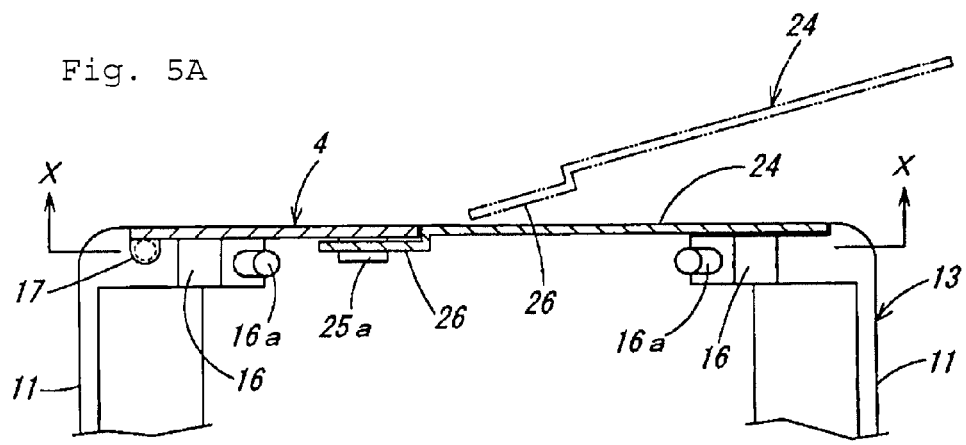
FIG. 5A is a sectional view in a state where an extension member is connected to the aerial mounting member.
Figure 5B:
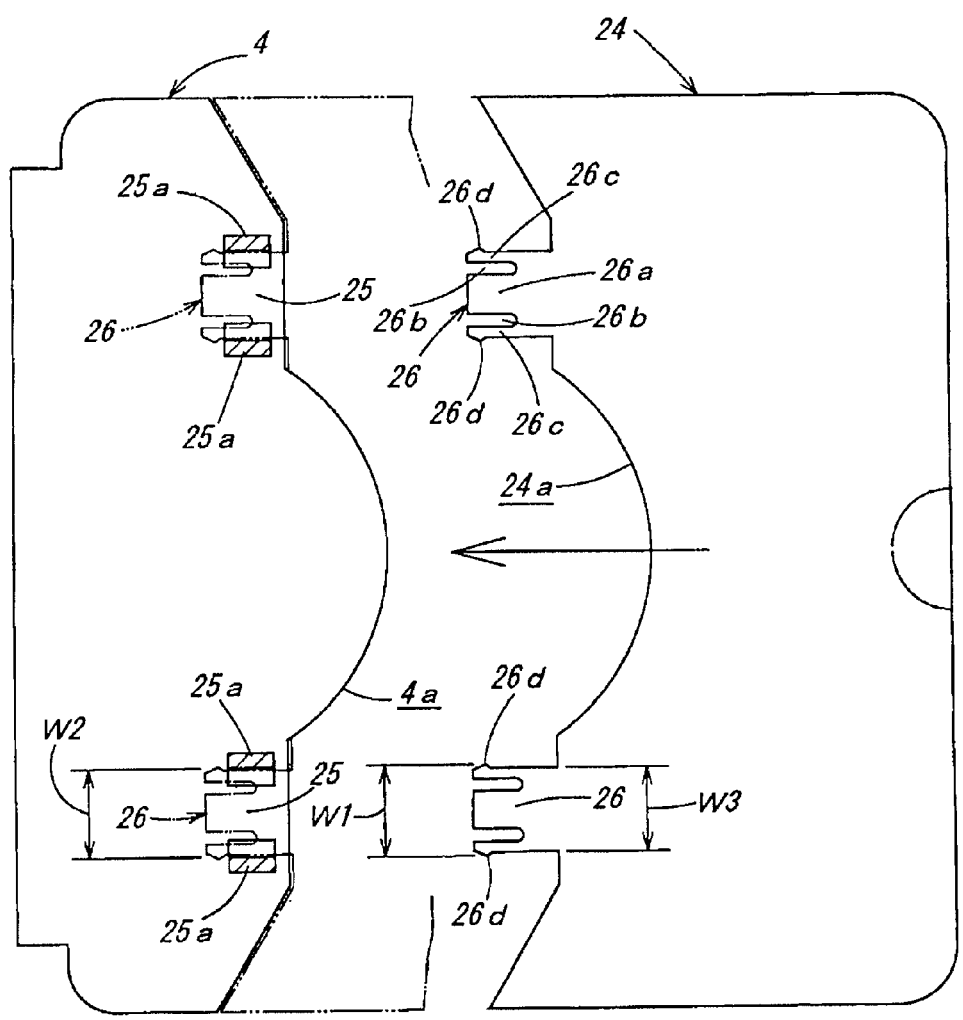
FIG. 5B shows the state where the extension member is connected to the aerial mounting member and is a sectional view taken along the line X-X in FIG. 5A.

The aerial mounting member 4 is made of plastic and is provided in such a manner as to cover a part of the upper opening O of the liquid bath 1 and leave the remainder open as described above. In a case of a measured object M too large to be mounted on the aerial mounting member 4, a plastic extension member 24 formed in such a size that covers the remainder of the opening O and extending the aerial mounting member 4 may be detachably connected to the distal end of the aerial mounting member 4 according to need. The extension member 24 is shown by an imaginary line in FIG. 1, and a detailed mounting structure thereof is shown in FIG. 5A and FIG. 5B. More specifically, to connect the extension member 24 to the aerial mounting member 4, a distal edge 24a of the extension member 24 is formed into a complementary shape corresponding to the shape of a distal edge 4o of the aerial mounting member 4 as shown in FIG. 5B. Additionally, the aerial mounting member 4 is provided with engagement-fitting recesses 25 as shown in FIGS. 3A, 5A, and 5B at both sides of the underside of the distal end. The extension member 24 is provided at the distal edge 24a thereof with engagement-fitting protrusions 26 insertably and removably engaged with and fitted to the engagement-fitting recesses 25 on the underside of the distal end of the aerial mounting member 4 in such a step-down fashion that top surfaces of the engagement-fitting protrusions 26 are flush with the underside of the extension member 24. It is noted that FIG. 5B is a sectional view taken along the line X-X in FIG. 5A and an illustration of the pivots 17 provided on the underside of the proximal end of the aerial mounting member 4 is omitted.

Each engagement-fitting recess 25 of the aerial mounting member 4 comprises a pair of L-shaped section pieces 25a arranged at a predetermined interval. Each engagement-fitting protrusion 26 of the extension member 24 is provided with a rectangular plate-shaped protruding piece 26a and notched grooves 26b at both sides of a distal end of the protruding piece 26a. Each notched groove 26b has an outside piece 26c whose outer side surface is formed with a mountain-shaped protrusion 26d. As shown in FIG. 5B, an outer dimension W1 between both mountain-shaped protrusions 26d of each engagement-fitting protrusion 26 is slightly larger than an inner dimension W2 between both L-shaped section pieces 25a of each engagement-fitting recess 25 (W1>W2). An outer dimension W3 between both lateral end surfaces of each engagement-fitting protrusion 26 is slightly smaller than the inner dimension W2 between both L-shaped section pieces 25a of each engagement-fitting recess 25 (W3<W2).

Accordingly, when the extension member 24 is connected to the aerial mounting member 4, the outside pieces 26c of each engagement-fitting protrusion 26 of the extension member 24 are seized from both sides and elastically deformed narrower. In this state, the engagement-fitting protrusions 26 are fitted to the counterpart engagement-fitting recesses 25 of the aerial mounting member 4. Then, as shown by an imaginary line in FIG. 5B, the outside pieces 26c of the engagement-fitting protrusions 26 elastically return with the distal ends of the engagement-fitting protrusions 26 protruding from the engagement-fitting recesses 25. The mountain-shaped protrusions 26d at both sides are engaged with the distal ends of the L-shaped section pieces 25a of the engagement-fitting recesses 25. In this state, the extension member 24 is connected and locked with the aerial mounting member 4. When the extension member 24 is detached, the distal ends of the engagement-fitting protrusions 26 protruding from the engagement-fitting recesses 25 are seized from both sides and elastically deformed narrower. In such a state, the extension member 24 is pulled toward the near side and then can be detached easily. It is noted that both ends of the proximal end of the extension member 24 are supported on the support arms 16 provided at the upper ends of adjacent columns 11 while the extension member 24 is connected with the aerial mounting member 4.

If the extension member 24 is connected to the distal end of the aerial mounting member 4 in the above manner, the upper opening O of the liquid bath 1 is covered entirely by the extension member 24 and the aerial mounting member 4. Thus, a measured object M too large to be mounted on the aerial mounting member 4 is placed on the aerial mounting member 4 and the extension member 24, whereby a measurement thereof can be carried out. Further, the above-described connection structure of the extension member 24 with respect to the aerial mounting member 4 allows the extension member 24 to be connected to the aerial mounting member 4 easily and readily according to need and also to be detached from the aerial mounting member 4 easily.

The measured object M comprising a noble metal is described in the above embodiment. However, besides that, the present invention can be employed in purity or physical property tests with the use of specific gravity of a wide variety of objects such as various metals, rubber, plastic, glass, ceramic, automotive parts, electronic parts, etc. In addition, in the above-described embodiment, the measured object receiving member 3 is hung and supported by the cable bodies 14 hung down from the upper ends of the columns 11 of the support frame body 13 in order to be housed within the liquid bath 1 in a non-contact manner. Instead of using such cable bodies 14, the measured object receiving member 3 may be configured to be integrally connected to the support frame body 13.

What is claimed is:
1. A specific gravity measuring apparatus comprising:
a liquid bath filled with a liquid;
a measured object receiving member which is supported within the liquid bath via a support means in a non-contact manner and into and out of which the liquid within the liquid bath can freely flow;
an aerial mounting member which is supported by the support means and on which a measured object is placed in order to measure gravity thereof in the air; and
a weighing apparatus receiving and supporting the measured object receiving member via the support means, the weighing apparatus being provided with a sensor converting a weight acted upon the measured object receiving member into an electrical signal and a measuring section measuring specific gravity of the measured object from an output of the sensor at a time when the measured object is placed on the aerial mounting member and an output of the sensor at a time when the measured object is submerged and placed on the measured object receiving member,
wherein the aerial mounting member is provided in such a manner as to cover a part of an opening at an upper part of the liquid bath and leave the remainder open but not to fully cover the opening, and the measured object having been placed on the mounting member can be dropped onto the measured object receiving member directly.

2. The specific gravity measuring apparatus according to claim 1, wherein the support means comprises:
- a support frame body integrally formed into a substantially square frame shape by four columns and transverse frames connecting the columns together;
- four cable bodies for hanging and supporting the measured object receiving member, the cable bodies being hung down from respective upper ends of the columns of the square frame-shaped support frame body; and
- a bottom frame body fixed on a receiving portion of the sensor of the weighing apparatus and supporting lower ends of the columns of the square frame-shaped support frame body.

3. The specific gravity measuring apparatus according to claim 2, wherein the columns of the square frame-shaped support frame body have upper ends provided with support arms respectively in a diagonal direction of the support frame body,
- the support arms have distal ends from which protruding portions are protruded, and to the protruding portions, upper ends of the cable bodies are fixed,
- the cable bodies have lower ends fixed to protruding portions provided at necessary places of an outer periphery of the measured object receiving member, and
- the four cable bodies hang and support the measured object receiving member.

4. The specific gravity measuring apparatus according to claim 1, wherein the measured object receiving member comprises a bottom plate and a peripheral wall projected along a peripheral edge of the bottom plate, and the bottom plate is provided with a plurality of through holes.

5. The specific gravity measuring apparatus according to claim 1, wherein the aerial mounting member has a proximal end pivotally fitted to the support means and is configured to change its posture between a horizontal posture of covering the part of the opening and a rising posture of rising from the horizontal posture.

6. The specific gravity measuring apparatus according to claim 1, wherein the aerial mounting member comprises a flat plate and a measured object mounting portion integrally projected along the flat plate from a center of a distal end of the flat plate and formed into a gentle concave dish-shape, and the measured object is placed on the gentle concave dish-shaped measured object mounting portion.

7. The specific gravity measuring apparatus according to claim 1, wherein the aerial mounting member has a distal end to which an extension member formed in such a size that covers the remainder of the opening and extending the aerial mounting member is detachably connected so as to be flush with the aerial mounting member.

8. The specific gravity measuring apparatus according to claim 2, wherein the measured object receiving member comprises a bottom plate and a peripheral wall projected along a peripheral edge of the bottom plate, and the bottom plate is provided with a plurality of through holes.

9. The specific gravity measuring apparatus according to claim 3, wherein the measured object receiving member comprises a bottom plate and a peripheral wall projected along a peripheral edge of the bottom plate, and the bottom plate is provided with a plurality of through holes.

10. The specific gravity measuring apparatus according to claim 2, wherein the aerial mounting member has a proximal end pivotally fitted to the support means and is configured to change its posture between a horizontal posture of covering the part of the opening and a rising posture of rising from the horizontal posture.

11. The specific gravity measuring apparatus according to claim 3, wherein the aerial mounting member has a proximal end pivotally fitted to the support means and is configured to change its posture between a horizontal posture of covering the part of the opening and a rising posture of rising from the horizontal posture.

12. The specific gravity measuring apparatus according to claim 2, wherein the aerial mounting member comprises a flat plate and a measured object mounting portion integrally projected along the flat plate from a center of a distal end of the flat plate and formed into a gentle concave dish-shape, and the measured object is placed on the gentle concave dish-shaped measured object mounting portion.

13. The specific gravity measuring apparatus according to claim 3, wherein the aerial mounting member comprises a flat plate and a measured object mounting portion integrally projected along the flat plate from a center of a distal end of the flat plate and formed into a gentle concave dish-shape, and the measured object is placed on the gentle concave dish-shaped measured object mounting portion.

14. The specific gravity measuring apparatus according to claim 2, wherein the aerial mounting member has a distal end to which an extension member formed in such a size that covers the remainder of the opening and extending the aerial mounting member is detachably connected so as to be flush with the aerial mounting member.

15. The specific gravity measuring apparatus according to claim 3, wherein the aerial mounting member has a distal end to which an extension member formed in such a size that covers the remainder of the opening and extending the aerial mounting member is detachably connected so as to be flush with the aerial mounting member.

* * * * *